United States Patent [19]

Brown et al.

[11] Patent Number: 5,597,578
[45] Date of Patent: Jan. 28, 1997

[54] TGF-β PROTEIN COMPOSITIONS FOR INHIBITION OF CELL PROLIFERATION

[75] Inventors: Dennis M. Brown; Edward Luck, both of Menlo Park, Calif.; Daniel R. Twardzik, Bainbridge Island; Anthony F. Purchio, Seattle, both of Wash.

[73] Assignees: Oncogen, Wash.; Matrix Pharmaceuticals, Calif.

[21] Appl. No.: 234,509

[22] Filed: Apr. 28, 1994

Related U.S. Application Data

[63] Continuation of Ser. No. 852,828, Mar. 13, 1992, abandoned, which is a continuation of Ser. No. 627,602, Dec. 11, 1990, abandoned, which is a continuation of Ser. No. 405,534, Sep. 11, 1989, abandoned.

[51] Int. Cl.⁶ ............... A61K 9/00; A61K 9/10; A61K 38/18; A61K 38/39
[52] U.S. Cl. ............ 424/422; 424/423; 424/426; 424/484; 514/12; 514/21; 530/350; 530/356; 530/399
[58] Field of Search ............... 530/399, 350, 530/356; 514/12, 21, 773, 774, 801; 424/484, 422, 423, 426

[56] References Cited

U.S. PATENT DOCUMENTS

| | | | |
|---|---|---|---|
| Re. 33,375 | 10/1990 | Luck et al. | 514/2 |
| 4,760,131 | 7/1988 | Sundsmo et al. | 514/801 |
| 4,774,228 | 9/1988 | Seyedin et al. | 514/21 |
| 4,837,285 | 6/1989 | Berg et al. | 530/356 |
| 4,950,483 | 8/1990 | Ksander et al. | 424/422 |
| 4,978,332 | 12/1990 | Luck et al. | 604/19 |
| 5,024,841 | 6/1991 | Chu et al. | 424/422 |

OTHER PUBLICATIONS

Mustoe et al., 1987, "Accelerated Healing of Incisional Wounds in Rates Induced by Transforming Growth Factor–β", Science 237: 1333–1336.

Pierce et al., Jul. 1989, "Platelet–Derived Growth Factor and Transforming Growth Factor–β Enhance Tissue Repair Activities by Unique Mechanisms", J. Cell. Biol. 109: 429–440.

Derynck et al. *J. Biol Chem* 261(10): 4377–4379 (1986).

*Primary Examiner*—Marianne P. Allen
*Attorney, Agent, or Firm*—Pennie & Edmonds

[57] ABSTRACT

Antiproliferative compositions are provided which are capable of sustained release of an antiproliferative agent, particularly a TGF-β, at a site proximal to a target cell. The compositions are effective in inhibiting proliferation of the target cell, particularly when used in combination with a vasoconstrictive agent.

14 Claims, 2 Drawing Sheets

TGF-β PROTEIN COMPOSITIONS FOR INHIBITION OF CELL PROLIFERATION

This is a continuation, of application Ser. No. 07/852,828, filed Mar. 13, 1992, abandoned; which is a continuation of application Ser. No. 07/627,602, filed Dec. 11, 1990, now abandoned; which is a continuation of application Ser. No. 07/405,534, filed Sep. 11, 1989, now abandoned.

FIELD OF THE INVENTION

This field relates to methods for inhibiting cell proliferation using a polypeptide having growth inhibitory activity in a physiologically acceptable vehicle comprising a proteinaceous matrix, particularly a collagen matrix.

BACKGROUND

The goal of any drug delivery system is to provide a therapeutic amount of a drug to the site in the body which is the intended target for drug therapy and to maintain a desired drug concentration for the time required to achieve a desired result. The two most important aspects of this goal are targeting of the drug to a specific organ or tissue (spatial placement) and controlling the rate of drug delivery (and hence the concentration at the target) to the target (temporal delivery).

The family of peptides known as transforming growth-factor type β (TGF-β), including TGF-β1 and TGF-β2, regulates cell growth and differentiation. These growth-regulatory polypeptides can both stimulate and inhibit cell proliferation, depending largely on the cell type. TGF-β1 and TGF-β2 have a common antiproliferative effect, for example, on epithelial cell growth, as well as a high degree of receptor cross-reactivity. Thus a degree of spatial placement may be achieved in controlling cell growth, in particular tumor cell growth, while minimizing effects on normal cells by use of such growth factors as antiproliferative agents. However, the half-life of the growth factor TGF-β, when administered by conventional means is on the order of 2 to 5 minutes due to, for example, degradative enzymatic activity or elimination via binding to serum binding proteins. Thus, the temporal delivery of these polypeptides is difficult to control.

To achieve spatial placement of a drug, a number of systems have been proposed. These include the use of targeted delivery systems such as nanoparticles, liposomes, and resealed erythrocytes, as well as the use of compositions which comprise a targeting portion, suck as an antibody to a specific cellular antigen, and a therapeutic portion, for example, a cytotoxic agent. Some spatial placement may also be achieved in specialized situations, such as the use of intraocular devices and intravaginal and intrauterine devices. Spatial placement may also be achieved by using drugs or naturally occurring compounds which have a higher affinity for one type of cell as opposed to another, for example, steroid or peptide hormones and congers thereof, which interact with specific receptors in/on the target cell.

Temporal delivery of a drug is not well controlled by conventional drug dosage forms (such as solutions, suspensions, capsules, tablets, emulsions, aerosols, films, ointments and suppositories). The rate-limiting step in delivery of drug to its target area is generally absorption of the drug across a biological membrane, such as the intestinal epithelium or the endothelial cell lining of the vasculature. One means of prolonging the bioavailability of an administered composition is to provide it in a form in which it may readily permeate across a cell membrane. An alternate means is to provide for nonimmediate release from the dosage form, so that release of the drug becomes the rate-limiting step in delivery of the drug to a specific target area. Nonimmediate-release delivery systems may take several forms, including sustained-release systems where the drug-delivery system slowly releases the drug over an extended period of time.

Use of a sustained-release system can improve the bioavailability of compounds such as polypeptides which are susceptible to enzymatic inactivation. The sustained-release system can be used locally, which can provide further for selective inhibition of cell proliferation since concentration of drug at the target site will be high, but the systemic concentration will be low. This is particularly advantageous for drugs which have a low therapeutic index since potential side effects are reduced by the-use of sustained-release systems. Lower total amounts of drug may be used, preferably less than the $LD_{50}$ of the drug. Thus it is of interest to develop methods and compositions for selective inhibition of cell proliferation by the use of a drug delivery system which provides both spatial placement and temporal delivery of growth factors having anti-proliferative activity. Such delivery systems can provide a more effective treatment yet achieve an antiproliferative effect at lower total drug concentrations.

Relevant Literature

U.S. Pat. Nos. 4,322,398; 4,347,234; 4,349,530; 4,391,797; and 4,619,913 describe implants and controlled release of drugs. Implantation of drugs in lesions is described in Maugh, *Science* (1981) 212:1128–1129; Macek et al., *Abstracts of Immunology*, 4109, p. 1053, Miyata et al., *Cancer Research* (1983) 43:4670–4675; McLaughlin et al., *Cancer Research* (1978) 38:1311–1316; and Bier et al., *Cancer* (1979) 44:1194–1200.

Purification and initial characterization of human TGF-β2 from an adenocarcinoma cell line is disclosed by Ikeda et al., *Biochemistry* (1987) 26:2406–2410 and from procine blood platelets by Cheifetz et al., *Cell* (1987) 48:409–415. Expression of mature and precursor TGF-β1 in Chinese hamster ovary cells is disclosed by Gentry et al., *Molec. and Cell Biol.* (1987) 7:3418–3427. Purification of TGF-β is reported by Gentry et al., *Molec. and Cell Biol.* (1988) 8:4162–4168.

A review of the family of compounds under the designation TGF-β is provided by Sporn et al., *Science* (1986) 233:532:534. The structure and functional relationship of CIF-B (cartilage-inducing factor B) to TGF-β is disclosed by Seydin et al., *J. Biol. Chem.* (1987) 262:1946–1949. See also Seydin et al., *Proc. Natl. Acad. Sci. USA* (1985) 82: 2267–2271; Twardzik, and Sherwin, *J. Cell. Biochem.* (1985) 28: 289–297.

SUMMARY OF THE INVENTION

Novel compositions and methods for their use are provided for inhibiting cell growth. The methods use polypeptide compositions comprising at least one TGF-β or fragment thereof characterized as having an antiproliferative effect on cells, wherein the polypeptide is provided dispersed in a proteinaceous matrix. For in vivo use, the compositions are implanted in the vicinity of the target cells. The polypeptide is continuously released from the matrix, creating a high concentration of polypeptide in the vicinity of the target cells. The composition is preferably used in conjunction with a vasoconstrictive agent. The method and treatment compositions are effective in inhibiting proliferation of cells, particularly neoplastic cells. Generally, substantially lower total amounts of polypeptide are required to inhibit cell proliferation than with conventional delivery systems.

DESCRIPTION OF THE SPECIFIC EMBODIMENTS

Figure 1:
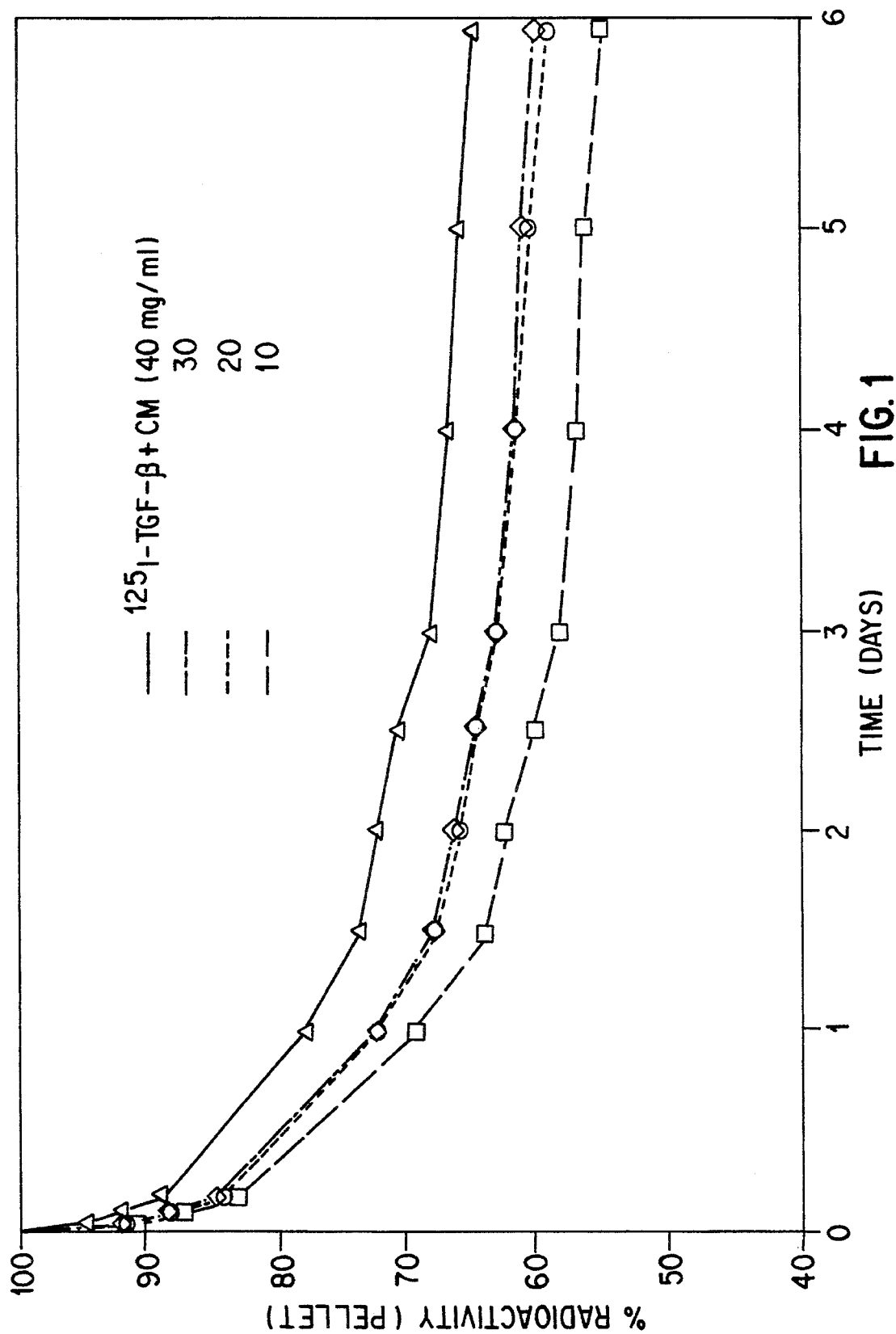
FIG. 1 shows the release of radioactively labelled TGF-β from CM-TGF-β (CM concentration: 40, 30, 20, or 10 mg/ml) as a function of time.

The present invention provides methods and compositions for inhibiting growth of cells such as neoplastic cells. The method relies on the local application of a treatment composition wherein the active moiety comprises at least one TGF-β or fragment thereof, wherein the TGF-β is dispersed in a proteinaceous matrix, particularly a collagen matrix. The matrix limits the diffusion of the TGF-β which may be implanted in the vicinity of the target cells thereby diminishing degradation, particularly enzymatic degradation which may occur from systemic exposure. The TGF-β is continuously released from the matrix, creating a higher concentration of TGF-β in the immediate vicinity of the neoplastic cells than in other areas. To inhibit dispersion of the drug away from the release site, the compositions may be administered in conjunction with a vasoconstrictive agent, such as epinephrine.

The sequence of the compositions of interest will usually be comparable to a sequence of a segment of the TGF-β molecule, including TGF-β precursor polypeptides. The compositions will include a sequence corresponding substantially to the portion of the molecule responsible for the observed biological effect of TGF-β for inhibiting proliferation of epidermal cells, in particular, keratinocytes.

The compositions of this invention will have as the active moiety at least about 8 amino acids, usually at least about 25 amino acids, more usually at least about 35 amino acids up to the full length of a TGF-β or TGF-β precursor polypeptide. Preferably, the composition comprises homodimers of TGF-β. By homodimers is intended a polypeptide comprising two identical amino-acid chains of at least 8 amino acids each. A preferred method of linkage of the two chains is via an interchain disulfide bond, where each chain includes at least one cysteine, although other linkages are possible.

TGF-β1 has the following sequence:

```
           5                10               15              20
A—L—D—T—N—Y—C—F—S—S—T—E—K—N—C—C—V—R—Q—L—

25               30               35              40
Y—I—D—F—R—K—D—L—G—W—K—W—I—H—E—P—K—G—Y—H—

45               50               55              60
A—N—F—C—L—G—P—C—P—Y—I—W—S—L—D—T—Q—Y—S—K—

65               70               75              80
V—L—A—L—Y—N—Q—H—N—P—G—A—S—A—A—P—C—C—V—P—

85               90               90             100
Q—A—L—E—P—L—P—I—V—Y—Y—V—G—R—K—P—K—V—E—Q—

105              110
L—S—N—M—I—V—R—S—C—K—C—S
``` and TGF-β2 has the following sequence:

```
                5                10               15
A—L—D—A—A—Y—C—F—R—N—V—Q—D—N—C 20               25               30
C—L—R—P—L—Y—I—D—F—K—R—D—L—G—W 35               40               45
K—W—I—H—E—P—K—G—Y—N—A—N—F—C—A 50               55               60
G—A—C—P—Y—L—W—S—S—D—T—Q—H—S—R 65               70               75
V—L—S—L—Y—N—T—I—N—P—E—A—S—A—S 80               85               90
P—C—C—V—S—Q—D—L—E—P—L—T—I—L—Y 95              100              105
Y—I—G—K—T—P—K—I—E—Q—L—S—N—M—I

110
V—K—S—C—K—C—S
```

The one-letter designations for the various amino acids are as follows: A=alanine; R=arginine; N=asparagine; D=aspartic acid; C=cysteine; Q=glutamine; E=glutamic acid; G=glycine; H=histidine; I=isoleucine; L=leucine; K=lysine; M=methionine; F=phenylalanine; P=proline; S=serine; T=threonine; W=tryptophan; Y=tyrosine; and V=valine.

It will be appreciated that the amino-acid sequence need not correspond exactly to the sequences given above, but may be modified by from 1 to 4 conservative or non-conservative substitutions, including deletions and insertions usually involving not more than about 1 amino acid, where the modifications may include D-amino acids, without significantly affecting the activity of the product. Therefore the subject polypeptides may be subject to various changes, such as insertions, deletions, and substitutions, either conservative or non-conservative, where such changes might provide for certain advantages in their use. By conservative substitutions is intended combinations such as G, A; V, I, L; D, E; N, Q; F, T; K, R; and S, Y, W.

Of particular interest are the naturally occurring TGF-βs and fragments thereof which are at least substantially free of other cellular components, usually at least about 90%, preferably 95%, more preferably 99% pure. The TGF-βs may be isolated from natural sources, or, as appropriate, synthesized or prepared by recombinant means. Of particular interest are mammalian, particularly primate, more particularly simian TGF-βs. They can be used individually, in combination with each other or in combination with other anti-proliferative compositions.

The polypeptides or fragments thereof may be conjugated to the proteinaceous matrix by conventional techniques. The cross-linking reagents used for this purpose are generally bifunctional molecules depicted as A—R'—B where R' is the moiety that connects two functional groups A and B which can react with groups such as amino ($NH_2$), carboxy ($CO_2H$) and sulfhydryl (SH) groups that may be present in the polypeptide or the solid support. The connecting portion, R', provides the cross-link with appropriate properties such as suitable spacer length or conformation.

The connecting portion, R' may be an alkylene chain, —$(CH_2—)_n$—, or a chain interspersed with other substituents, —$(CH_2)_mQ(CH_2)_n$—. The substituent Q may be unsaturated groups such as —CH═CH— and —C≡C—; aromatic groups such as phenylene, —$C_6H_4$— (linked in ortho, meta, or para fashion); heteroaromatic groups such as those derived from pyridine, imidazole, indole; or polycyclic forms of aromatic and heteroaromatic ring systems. The ring systems may possess additional substituents, e.g. halogen, methyl, and nitro, but are not limited to these. Likewise, additional substituents may be present, replacing one or more H in the methylene chains —$(CH_2)_m$— and —$(CH_2)_n$—.

Cross-linking reagents in which A and B are the same are called homobifunctional reagents; those in which A and B are different are called heterobifunctional reagents. If A and B are different, the reaction to cross-link the two components—the peptide and the support—is generlly carried out step-wise. Step-wise reaction is also possible where A and B are the same if one group is activated first and the other left unactivated or in a blocked or protected form. When A and B are the same, simultaneous reaction with the two components is possible. This is more direct, but may be less selective than a step-wise sequence of reaction.

For cross-linking with amines, the reactive functional groups A and B may be carboxylic acids (activated in some way), aldehydes or alkylating agents.

When A is a carboxylic acid, there are many ways to activate this for reaction with amines to form amides. This is generally discussed in organic chemistry texts such as that by F. A. Carey and R. J. Sundberg, *Adanced Organic Chemistry* (1983) 2:118 and following, and thoroughly discussed in books dealing with peptides, such as those by E. Gross and J. Meienhofer, *The Peptides* (1979) 1 and by M. Bodanszky, *Peptide Chemistry* (1988). A list of peptide bond forming reagents is given in the glossary of Pettit's book (G. R. Pettit, *Synthetic Peptides* (1970) 1). Only some general ways of activation of carboxyl groups are discussed here.

The groups A═$CO_2H$ can be activated to

and reacted with amino groups to form a peptide bond:

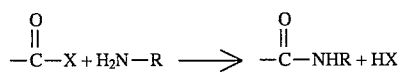

Carboxylic acids can be activated to acyl halides and pseudohalides

where X═Br, Cl, CN, $N_3$) mixed anhydrides and activated esters. Activation by addition reactions using carbodiimides and isoxazolium reagents is also used.

In mixed anhydrides, the x of

is derived from another carboxylic acid, carbonic acid, a sulfonic acid, or a phosphorous-containing acid. Many examples are possible (see references mentioned); these examples are representative:

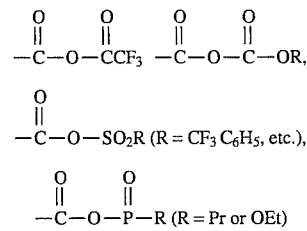

In active esters,

has X═OR which may be derived from very electronegative phenols (R═$C_6F_5$, $C_6Cl_5$, $C_6H_3(NO_2)_2$, etc.) or N-hydroxy compounds such as N-hydroxysuccinimide and N-hydroxybenzotriazole.

Activation of carboxyl groups by carbodiimides proceed through an intermediate which reacts with the amino group:

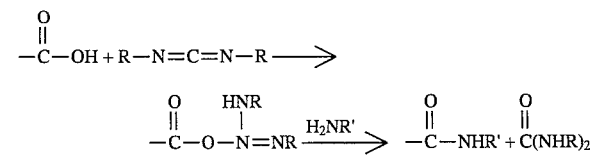

If the intermediate is formed in the presence of N-hydroxysuccinimide, or N-hydroxybenzotriazole, the an active ester is presumably formed (see above) and this reacts with the amino group.

When A is an aldehyde, the cross-linking reagent is a dialdehyde. One type is represented by O═CH—$(CH_2)_n$—CH═O. This reacts with the polypeptide ($R^2NH_2$) and the support ($R^3NH_2$) in the following way: $R^2NH_2+R^3NH_2+$ O═$CH(CH_2)_n$CHO→$R^2N$═$C(CH_2)_nCH$═$NR^3+2H_2O$. Glutaraldehyde, with n=2, is a common cross-linking reagent. When n is increased, the spacer between the coupled peptide and the solid support becomes longer. Generally, there is an optimum range for the spacer length.

The dialdehydes may also be derived from aromatic or heteroaromatic compounds as shown by this example of phthalaldehyde.

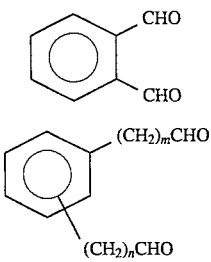

Substitution in ortho, para, or meta positions, together with different lengths of side chains is shown in structure 2.

The benzene rings in 2 may be replaced by other ring systems that are polycyclic or heterocyclic. Other substituents, e.g., halogen, nitro, alkyl, may be on these ring systems.

Although formaldehyde is not a bifunctional aldehyde, it can react with two amino groups, and is used as a cross-linking reagent.

$$R^2NH_2 + R^3NH_2 + CH_2O \rightarrow R^2NH\text{—}CH_2\text{—}NHR^3 + H_2O$$

Bifunctional cross-linking reagents derived from alkylating agents (A—R'—B where A and B are alkylating groups) are not commonly used in cross-linking peptide, although they are used in cross-linking other types of polymers and supports. Two examples are sulfonate esters and epoxides as shown by these example:

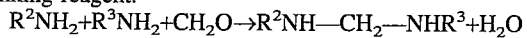

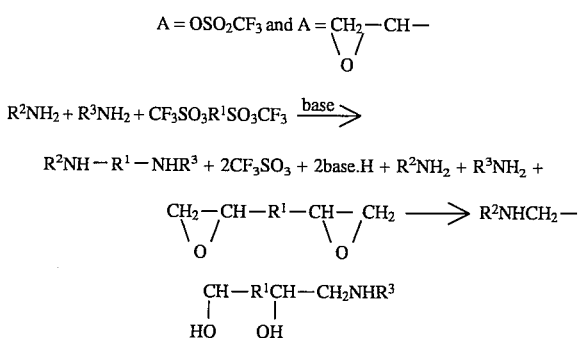

These reagents can also react with sulfhydryl groups:

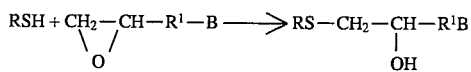

Other functional cross-linking reagents that can react with sulfhydryl groups can have A=maleimido or A=ICH$_2$C—:

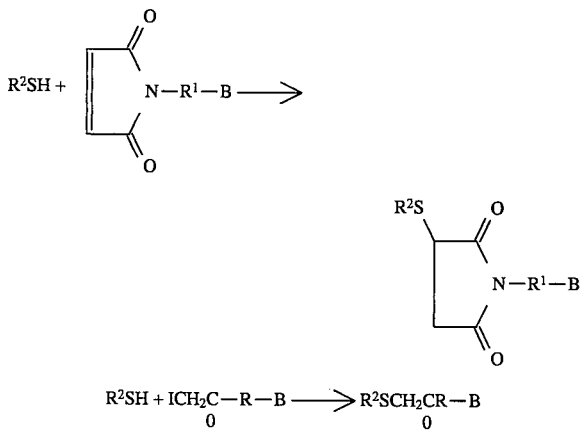

Bifunctional cross-linking reagents that can react with carboxyl groups on the components to be coupled (the peptide or the support) can have A=amino:

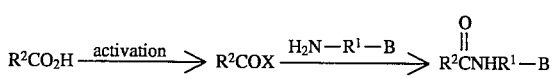

If B is also amino, or if there are amino groups in the component (polypeptide or support) being coupled, these amino groups must be blocked or protected before reaction and later deblocked.

Some bifunctional cross-linking reagents are available commercially. For example, a series of homobifunctional (example, cpd 3) and heterobifunctional (example, cpd 4) cross-linking reagents are available from Pierce Chemical Company.

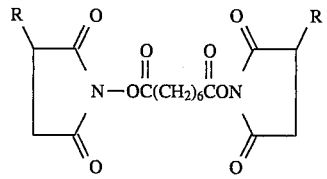

3a, R = H
3b, R = SO$_3$Na

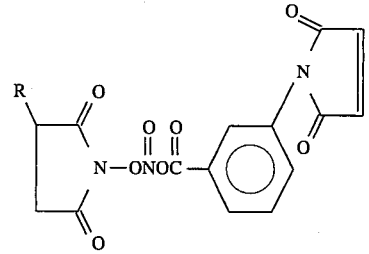

4a, R = H
4b, R = SO$_3$Na

In cross-linking two components-peptide and support-there is the possibility of forming intracomponent cross-links instead of the desired intercomponent ones. Such side reactions can be minimized by the choice of reagents and reaction conditions, and by the use of removable blocking groups.

Various solid supports may be used for preparation of the subject compositions. The subject compositions are amorphous, injectable and viscous, so as to substantially retain a localized position without significant flow from the site of administration. The compositions can flow under moderate pressure, but will not move significantly after being positioned at a particular site. The proteinaceous matrix will be capable of binding the antiproliferative polypeptides covalently or non-covalently, without affecting their therapeutic effect, while serving to retain the active agents at the site of introduction or retarding transfer of the active agents from the site of introduction.

Preferably, the composition will be comprised of a significant amount of the proteinaceous matrix to provide the desired composition characteristics. The matrix may be individual peptides or combinations of peptides or proteins, e.g., structural proteins such as collagen and fibrinogen, or albumin or other protein, which provide for stable placement, or combinations thereof. Of particular interest are collagen, fibrinogen and derivatives thereof.

Proteinaceous matrices in the drug delivery system comprising about 5 weight percent, preferably at least about 10 weight percent, and up to 50 weight percent or more of fibrinogen, are of particular interest when used in combination with thrombin or its enzymatic equivalent. In this way fibrinogen is enzymatically modified to fibrin to enhance the non-migratory property of the composition while forming a matrix of fibrils to further stabilize the composition.

The thrombin may be mixed with a fibrinogen containing proteinaceous composition from a time immediately prior to use or shortly after injection. The amount of thrombin employed (about 1 to 1000 IU/mg) generally will range from about 0.1 to 10 weight percent of the fibrinogen present, depending upon the time of use, the rate desired for solid matrix formation, the amount of other components, the effect of the drug on thrombin activity, and the like.

The proteinaceous, particularly collagenous or fibrinogen-containing, material which is used may be derived from any mammalian host source, such as bovine, porcine or human, or may be prepared, as available, by other techniques, e.g., recombinant DNA techniques. The collagen employed may be natural collagen or may be modified, such as tropocollagen, atropocollagen, or the like. The collagen may be non-immunogenic, immunogenic, or only slightly immunogenic.

Various methods for preparing collagen or derivatives thereof in purified form for administration to a mammalian host are known in the literature. These methods may be found in such patents as U.S. Pat. No. 3,949,073 and references cited therein. Of interest is bovine collagen which is purified and is obtained from young cows or calves. Purification will normally involve dispersion or precipitation from various media, e.g., dilute acetic acid. In some situations xenogeneic collagen is employed to enhance an immunogenic response in the area of injection or immunogenic adjuvants may be employed.

In addition, the drug(s) can be employed encapsulated in liposomes or other controlled rate release compositions, which are included in the proteinaceous composition, so as to provide for separate and distinct rates of release of the drug. In this way, multiphasic compositions can be prepared, so as to provide for sustained release of the drug over long periods of time. Formation of liposomes with inclusion of various materials is described in Papahadjopoulos (1978) *Annals of the N.Y. Academy of Science,* 308; Gregoriadis and Allison (1980) *Liposomes in Biological Systems* (John Wiley and Sons); Leserman et al., *Nature* (1981) 293:226–228; Barhet et al., *Supramol. Struct. Cell Bio. Chem.* (981) 16:243–258; and Heath et al., *Science* (1980) 255:8015–8018. Alternatively, other methods of encapsulation can be employed where the drug is encapsulated in a biodegradable substance, where the rate of release is related to the thickness of the biodegradable coat.

The subject compositions comprising the proteinaceous matrix and the antiproliferative agent may be used in vitro or in vivo. For in vitro use, they can be used for selectively inhibiting proliferation of cells which are sensitive to the growth inhibitory effects of a TGF-β. The subject compositions can be prepared so that the amount of the active moiety which diffuses from the proteinaceous matrix is an amount sufficient to inhibit proliferation of undesired sensitive cells. The amount of active moiety released from the matrix per unit time may be varied and can be optimized for particular situations by modifying the amount or concentration of either the active moeity or the proteinaceaus matrix in the composition.

In vivo, the composition may be implanted directly in an area of hyperproliferation of cells or in a cellular lesion area, or may be implanted at a site immediately adjacent to such areas, so as to provide for a higher concentration of the active moiety in the immediate vicinity of the proliferating cells than in surrounding tissue. The amount of the active moiety released from the solid support can be varied, depending upon the nature of the cell growth which is to be modulated, the size of the cell population, the sensitivity of the cell to the active moiety, the effectiveness of the active moiety and the like. The amount of TGF-β bound to the solid support is generally between 1 ng/ml and 10 mg/ml of collagen (10–40 mg/ml), more usually 10 ng to 1 mg/ml, preferably 100 ng to 100 μg/ml. The amount of release of TGF-β from the solid support is usually from about 1% to about 60% for the initial 4–6 hours of release, and reaches a steady state amount of release of about 1% to 20% per day thereafter.

The TGF-beta associated with the matrix may be used individually or in combination with other antiproliferative agents, depending upon the nature of the agent, the type of cells to be inhibited, and whether cooperative action is pharmacologically indicated. The subject composition can be further modified, by modifying the active moiety, particularly by bonds which allow for enzymatic cleavage, e.g., hydrolysis, or by introducing materials into the composition which will aid in the maintenance of or the retention of the active moiety at the site of introduction.

Various techniques can be used for diminishing migration of the antiproliferative agent away from the proteinaceous matrix, for example, by coupling the agent with specific ligands, such as lipids, phospholipids, peptides, amino acids, sugars, or the like. These modifications will depend upon the individual agent, varying the solubility of the agent in the aqueous medium and providing for covalent or non-covalent interactions with the proteinaceous matrix. In addition, various physiologically acceptable bulking agents or concentrating agents may be employed, which serve to provide for drug and matrix interactions, with a resulting reduction in the rate of drug release. Illustrative materials include inorganic substances such as hydroxyapatite and organic substances such as carbohydrates, e.g., agarose, cellulose, mucopolysaccharides; hyaluronic acid; chondroiton sulfate; and the like.

Other drugs for use in combination with the antiproliferative agents are drugs which retard diffusion away from the site of implantation of the antiproliferative agent. This serves to reduce physiological insult and enhance therapeutic gain. Of particular interest as antidiffusants are agents which restrict the regional vasculature, either as to growth and/or passage opening, e.g., vasoconstrictive or sympathomimetic agents. These agents may include catecholamines, e.g., epinephrine and norepinephrine; ergot alkaloids; prostaglandins; angiotensin, or the like. Other agents which can affect tissue architecture include enzymes which injure the stroma, such as the peptidases e.g. papain, chymopapain, trypsin, amylase, collagenase and chymotrypsin; or agents affecting cellular permeability may be employed, such as non-ionic detergents, e.g., Tween 80; amphotericin B; dimethylsulfoxide; and anesthetics, such as procaine. Other agents which may find use include those involved in DNA repair inhibition and DNA or RNA synthesis inhibition.

Of particular interest as target cells are tumor cells which are sensitive to the growth inhibitory effects of the active moiety (antiproliferative growth factor) associated with the matrix. The subject compositions find particular use with carcinomas which are readily accessible for implantation and which are sensitive to the active moiety, including lung cancer, squamous cell and basal cell carcinoma, breast cancer, melanoma, as well as tumors of endothelial and fibroblast origins such as sarcomas, e.g. osteosarcoma, and lymphoma.

As already indicated, the ratio of dry materials in the composition may vary widely. However, the amount of protein matrix material in the drug delivery system will usually be not less than 30% and not greater than about 95%, generally ranging from about 40% to 90%, more usually ranging from about 50% to 90% by weight. Of this, preferably 10% to 100% will be collagen and/or fibrinogen. The antiproliferative drug(s) will normally be a liquid or a solid, or provided in solid form and will generally range from at least about 0.0001% by weight to up to about 5% by weight, more usually being from about 0.001% to 1% by weight, generally being from about 0.001% to 0.1% by weight of the proteinaceous material.

Other ancillary additives or agents will vary in total amount from about 0.005 to 15, usually from about 0.01 to 10 weight percent of the dry weight of the total composition.

The composition is uniformly dispersed in a physiologically acceptable aqueous medium, such as saline, phosphate buffered saline, distilled water, water for injection, etc. The aqueous medium will be sufficient to provide for an amorphous dispersion capable of flowing under mild pressure. Usually, the liquid aqueous medium will be at least 90 weight percent of the entire composition, more usually at least 95 weight percent, and not more than about 99.8 weight percent, usually not more than about 99.5 weight percent, so as to provide a flowable mixture. The amount will vary depending upon the nature of the drug(s), the nature of the matrix material, the presence of other materials, and the like. The concentration of protein in the aqueous medium will range from about 5 to 75 mg/ml.

In addition to the major components, a number of minor components may also be included for a variety of purposes. These agents will for the most part impart properties which protect the stability of the composition, control the pH, or the like. Illustrative agents include phosphate or acetate buffers, methyl or propyl paraben, polyethylene glycols, etc. These agents generally will be present in less than about 2 weight percent of the total composition, usually less than about 1 weight percent, and individually may vary from about 0.001 weight percent to about 1 weight percent.

As already indicated, in some instances the drug will be encapsulated particularly in liposomes. Liposomes are prepared from a variety of lamellar-forming lipids including phospholipids, e.g., phosphatidylcholine, phosphatidylethanolamine, etc., gangliosides, sphingomyelins, steroids, e.g., cholesterol, etc. Usually, the weight of the lipids in relation to the weight of drug will range from 1 to 5 liters of entrapped drug per mole of amphipathic lipid.

The composition can be prepared by combining the various components in a sterile environment. The matrix will be provided in a convenient form, usually admixed with at least a portion of the total aqueous medium to be employed. The composition will be sufficiently workable that, upon admixture with the other agents, a uniform dispersion can be obtained. When collagen or a derivative thereof is used, the collagenous material will normally be provided [a monomeric or polymeric, particularly di or trimeric, form] or as a uniform dispersion of collagen fibrils in an aqueous medium, where the collagenous material will be from about 5 mg/ml to not more than 100 mg/ml, usually not more than 75 mg/ml. The drug may then be added to the collagenous dispersion with agitation to ensure the uniform dispersion of the drug in the resulting mixture. Other materials, as appropriate, may be added concomitantly or sequentially. After ensuring the uniform dispersion of the various components in the mixture, the mixture may be sterilized and sealed in appropriate container.

Sterilization will usually be achieved using asceptic techniques and asceptic conditions to admix all sterile components.

EXPERIMENTAL

Collagen for preparing the collagen matrix was obtained essentially as described in U.S. Pat. No. 3,949,073, and references cited therein, which disclosures are hereby incorporated by reference. To prepare CM-TGF-$\beta$, a pH neutral composition comprising 6.5% (w/v) collagen was first prepared. Just prior to use, or within one hour of use, TGF-beta (Oncogen) was prepared, according to the manufacturer's instructions, by resuspension in a phosphate buffered solution at a concentration to provide the desired final ratio of TGF-beta: collagen, generally, 1 ng/ml to 10 mg/ml of collagen. The TFG-beta and collagen were then mixed using a dual Luerlock mixing device. One syringe was filled with collagen and the other with TGF-beta, and the contents of the two syringes mixed by repeatedly pushing back and forth at room temperature, for approximately 20 strokes, until the suspension was homogeneous as determined by visual inspection. The CM-TGF-beta Was stored for up to one hour at 4° C. or room temperature until use.

EXAMPLE 1

Release of TGF-$\beta$ from Collagen Matrix (CM) in Vitro $^{125}$I-TGF-$\beta$ (2 $\mu$Ci) was added to cold TGF-$\beta$ such that a final TGF-$\beta$ concentration of 400 ng/ml in concentrations of CM of 10, 20, 30 or 40 mg/ml were obtained.

Approximately 0.7 ml of each formulation of CM containing $^{125}$I-TGF-$\beta$ was placed in the bottom of disposable plastic test tubes and the radioactivity of the CM-TGF-$\beta$ was determined in a gamma counter. Then approximately 1.4 ml of phosphate buffered saline (PBS) was carefully layered over the CM-TGF-$\beta$ pellet in the test tube. As a function of time, the PBS was removed from the test tube. The CM-TGF-$\beta$ pellet was recounted at each time point.

Release of $^{125}$I-TGF-$\beta$ from the CM carrier appeared to be influenced by the CM concentration. Initial release of TGF-$\beta$ occurred more quickly over the first day for the formulation containing 10 mg/ml CM as compared to the other formulations studied. The steady-state release of TGF-$\beta$ from all formulations seemed to stabilize such that approximately 1% of TGF-$\beta$ was released per day for the balance of the six days of the experiment for all groups tested. These data are shown in FIG. 1.

EXAMPLE II

Activating and Efflux Kinetics of TGF-$\beta$ from Collagen Matrix (40 mg/ml).

The biological activity and rate of release of TGF-$\beta$ from a bovine collagen carrier was evaluated as follows.

Five hundred ng simian TGF-$\beta$ (Oncogen) in 0.4 ml PBS were mixed with 0.8 ml of Collagen Matrix (CM) (65 mg/ml) (Matrix Pharmaceutical, Inc., Menlo Park, Calif.), yielding a final formulation containing 417 ng/ml TGF-$\beta$ and CM (43 mg/ml). Five hundred ng TGF-$\beta$ in 1.2 ml PBS, yielding 417 ng/ml TGF-$\beta$ in PBS, served as the control.

One ml of TGF-$\beta$ and CM was placed in the bottom of a test tube. Two ml of Dulbecco's minimal essential medium (DMEM) was carefully layered on top of the formulation. The control was diluted similarly.

At each time point, a 300 $\beta$l aliquot of the supernatant was collected. The time points were as follows:

0' 10' 20' 30' 1Hr 3Hr 8Hr 17Hr 24Hr 72H

Figure 2:
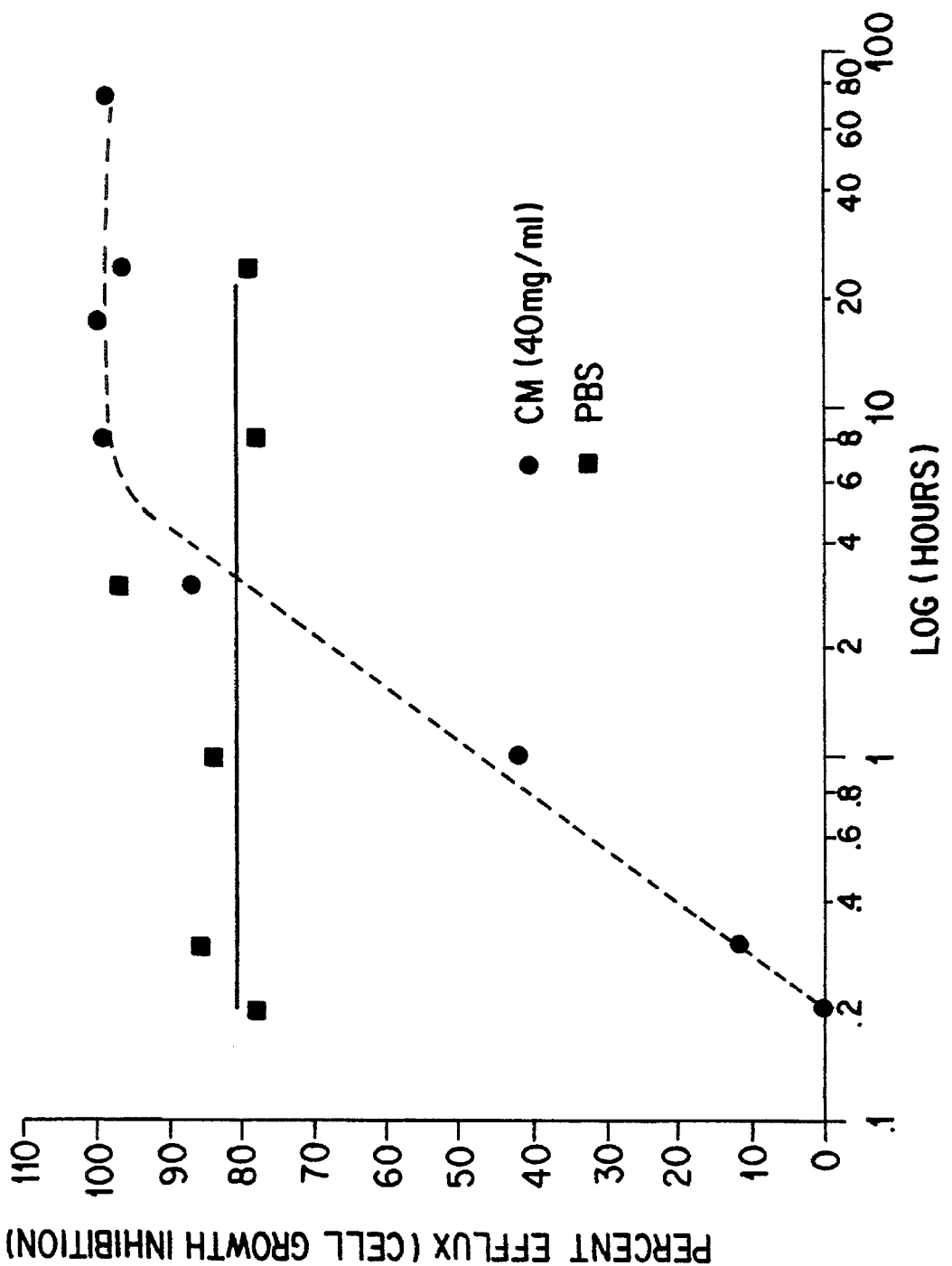
FIG. 2 shows the percentage efflux of TGF-β from CM-TGF-β (40 mg/ml CM concentration) as measured by inhibition of cell growth as a function of time.

From each sample, a 50 $\mu$l aliquot was removed and added to each of 3 wells of a multi-well tissue culture plate containing 3,000 A549 human lung cells per well. Three to five days later, the wells were pulse-labeled with $^{125}$I-thymidine to measure the amount of incorporation of thymidine into actively proliferating A549 cells. The cells were incubated at 37° C. in 5% $CO_2$— 95% air. All steps and preparations were carried out under aseptic conditions. The results show that TGF-$\beta$ was slowly released from the CM in log-linear fashion through the first 8 hours. The increasing concentrations of TGF-β released from the CM resulted in increased cell growth inhibition when tested against the TGF-β sensitive A549 cells, with sufficient drug being released within one hour to cause a 50% inhibition of cell growth. Full inhibition was observed after 8 hours and remained constant for the entire 72 hours of the experiment. TGF-β in PBS without the CM carrier inhibited approximately 80% of the cell proliferation activity throughout the entire experiment. These data are shown in FIG. 2.

EXAMPLE III

Effect of Collagen Matrix (CM)-Mediated Delivery of TGF-β1 on the Growth of A549 Human Lung Tumor Cell in Nude Mice Male nude mice (Balb/c–nu+/nu+) at 12 weeks of age were injected in the dorsal neck region subcutaneously with $1.3 \times 10^6$ human lung carcinoma cells (A549) in a volume of 0.2 ml of PBS. Within 20 days, palpable tumors (>10 mm$^3$–3×3×1 mm) had developed in approximately 80% of the animals. Tumor size was measured with calipers in three diameters. The tumor-bearing animals were then randomly assigned to different treatment groups. Day 1 of treatment corresponds to the first day animals were treated after measurable tumors developed. TGF-β1 was purified to homogeneity from Chinese hamster ovary cells expressing recombinant simian TGF-β1 and stabilized with a 10-fold excess of bovine serum albumin (BSA). Total amounts of each factor administered for the duration of this particular experiment were as indicated under "Treatment."

The efficacy of CM-mediated delivery of TGF-β1 peritumorally relative to a saline vehicle was evaluated as follows. Experimental groups (see Table 1) received TGF-β1 at a dose of either 2 μg administered peritumorally once or 400 ng administered 5 times at intervals of 2–3 days. An evaluation of CM-TGF-β1 with or without the vasoactive modifier epinephrine were studied in comparison with the carrier alone (CM(30 mg/ml)), phosphate buffered saline (PBS) alone or CM (30 mg/ml) alone. The endpoint was taken at day 16 and the percent of the treated tumor volumes to that of the untreated control tumors was established, as shown in Table 1.

TABLE 1

Effect of TGF-β1 Administered Either Alone or in Combination with CM and Epinephrine on Growth of A549 Tumors in Nude Mice

| Group | Treatment | No. Mice | Tumor Growth[1] |
|---|---|---|---|
| 1 | Saline Control | 5 | 100 |
| 2 | CM (30 mg/ml) 0.1 ml s.c.[2] × 1 | 5 | 84 |
| 3 | TGF-β (400 ng/0.1 ml) s.c. × 5 (2–3 days apart) | 5 | 57 |
| 4 | TGF-β (2 μg/0.1 ml) s.c. × 1 | 5 | 72 |
| 5 | TGF-β1 (2 μg/0.1 ml) + CM, s.c. × 1 | 5 | 84 |
| 6 | TGF-β (2 μg/0.1 ml) + CM + Epi (25 μg/0.1 ml) s.c. × 1 | 5 | 63 |

[1]Percent of saline control tumor volume on Day 16.
[2]s.c. indicates subcutaneous injection peritumorally.

As shown above, the most effective regimen for TGF-β1 was to administer the TGF-β1 peritumorally in five doses of 400 ng dose each at 2–3 day intervals (Group 3). The results further suggest that repeated exposure of the tumor cells to TGF-β1 is more effective than a single administration of a higher dose (2 μg) (Group 4). However, when TGF-β1 was given with CM, in combination with the vasoactive modifier epinephrine (Group 6), a single injection resulted in suppression of tumor growth similar to that observed with multiple small doses of TGF-β1 (Group 3). The tumor was presumably being exposed to a chronic low dose of TGF-β1 as TGF-β1 was released from the CM to the site.

The above results demonstrate that CM-TGF-β1 particularly in combination with a vasoactive agent is effective in inhibiting cell proliferation. As evidenced by the above disclosure, compositions are described which provide for slow release of an antiproliferative agent in the proximity of a target cell.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. In a method for inhibiting proliferation of cells sensitive to TGF-β1 by contacting said cells with an antiproliferative composition, the improvement which comprises:

an antiproliferative composition consisting essentially of an amorphous, viscous, injectable proteinaceous matrix comprising a uniform dispersion of collagen fibrils in a physiologically acceptable aqueous medium and wherein said matrix contains TGF-β1 in an amount sufficient, when released from said matrix, to inhibit proliferation of said cells.

2. The method according to claim 1, wherein said TGF-β1 is simian TGF-β1.

3. The method according to claim 1, wherein said TGF-β1 is at a concentration of from about 1 ng/ml to about 10 mg/ml, and the concentration of said collagen is about 10 to 40 mg/ml.

4. The method according to claim 1, wherein said matrix further contains a vasoconstrictive agent in an amount sufficient to retard diffusion of said TGF-β1 away from said collagen matrix.

5. The method according to claim 4, wherein said vasoconstrictive agent is epinephrine.

6. The method of claim 1 wherein the collagen is bovine skin collagen.

7. The method of claim 1 wherein the TGF-β1 is uniformly dispersed in said matrix.

8. A pharmaceutical composition for inhibiting cell proliferation consisting essentially of an amorphous, viscous, injectable proteinaceous matrix comprising a uniform dispersion of collagen fibrils in a physiologically acceptable aqueous medium and wherein said matrix contains TGF-β1 in an amount sufficient, when released from said matrix, to inhibit proliferation of said cells.

9. The composition of claim 8, wherein the collagen is at a concentration of from about 10 mg/ml to about 40 mg/ml and the TFG-β1 is at a concentration of from about 1 ng/ml to 10 mg/ml.

10. The composition of claim 9, wherein the TGF-β1 is simian TGF-β1.

11. The composition of claim 8 wherein said matrix further contains a vasoconstrictive agent in an amount sufficient to retard diffusion of said TGF-β1 away from said collagen matrix.

12. The composition of claim 11, wherein said vasoconstrictive agent is epinephrine.

13. The composition of claim 8 wherein the collagen is bovine skin collagen.

14. The composition of claim 8 wherein the TGF-β1 is uniformly dispersed in said matrix.

* * * * *